United States Patent
Addonizio et al.

(10) Patent No.: US 7,329,277 B2
(45) Date of Patent: Feb. 12, 2008

(54) STENT HAVING HELICAL ELEMENTS

(75) Inventors: Scott J. Addonizio, Fort Lauderdale, FL (US); David L. Camp, Jr., Hillsboro Beach, FL (US); Gary J. Becker, Miami, FL (US); John D. Pazienza, Pompano Beach, FL (US)

(73) Assignee: OrbusNeich Medical, Inc., Fort Lauderdale, FL (US)

( * ) Notice: Subject to any disclaimer, the term of this patent is extended or adjusted under 35 U.S.C. 154(b) by 168 days.

(21) Appl. No.: 10/014,705

(22) Filed: Dec. 11, 2001

(65) Prior Publication Data

US 2002/0095206 A1 Jul. 18, 2002

Related U.S. Application Data

(63) Continuation-in-part of application No. 09/511,481, filed on Feb. 23, 2000, now Pat. No. 7,108,714, which is a continuation of application No. 09/094,402, filed on Jun. 10, 1998, now Pat. No. 6,117,165.

(60) Provisional application No. 60/254,688, filed on Dec. 11, 2000.

(30) Foreign Application Priority Data

Jun. 13, 1997 (EP) .................................. 97201799
May 6, 1998 (EP) .................................. 98201446

(51) Int. Cl.
*A61F 2/06* (2006.01)
(52) U.S. Cl. ..................................... 623/1.22; 623/1.15
(58) Field of Classification Search ................. 623/1.1, 623/1.15, 1.16, 1.22, 11.11, 12, 1.3; 606/191–198
See application file for complete search history.

(56) References Cited

U.S. PATENT DOCUMENTS

| 5,449,373 | A | | 9/1995 | Pinchasik et al. |
| 5,697,971 | A | * | 12/1997 | Fischell et al. ............ 623/1.15 |
| 5,733,303 | A | | 3/1998 | Israel et al. |
| 5,843,120 | A | | 12/1998 | Israel et al. |
| 5,895,406 | A | | 4/1999 | Gray et al. |

(Continued)

FOREIGN PATENT DOCUMENTS

| EP | 0884029 | 12/1998 |
| EP | 0968689 | 1/2000 |

*Primary Examiner*—Thomas Sweet
*Assistant Examiner*—Jonathan R Stroud
(74) *Attorney, Agent, or Firm*—White & Case LLP

(57) ABSTRACT

An expandable stent comprised of a plurality of helical segments is disclosed. In one embodiment, the stent is generally cylindrical in shape having a cylindrical axis, and comprises a first and second set of helical segments. The helical segments in the first set are substantially parallel and have a first pitch forming a first helical angle with respect to the cylindrical axis. The helical segments in the second set are also generally parallel to each other and form a second pitch that differs from the first pitch, thereby forming a second helical angle with respect to the cylindrical axis. In an alternative embodiment, the stent comprises one set of helical segments and a plurality of circumferential elements that are joined together by the helical segments to form a plurality of cylindrical elements which are joined together to form a stent body. The stent may also have endzones.

34 Claims, 12 Drawing Sheets

U.S. PATENT DOCUMENTS

| | | | |
|---|---|---|---|
| 5,913,897 A * | 6/1999 | Corso et al. | 623/1.15 |
| 5,972,018 A | 10/1999 | Israel et al. | |
| 5,980,552 A | 11/1999 | Pinchasik et al. | |
| 6,059,811 A | 5/2000 | Pinchasik et al. | |
| 6,254,632 B1 * | 7/2001 | Wu et al. | 623/1.15 |
| 6,270,524 B1 * | 8/2001 | Kim | 623/1.15 |
| 6,331,188 B1 * | 12/2001 | Lau et al. | 623/1.13 |
| 6,432,132 B1 * | 8/2002 | Cottone et al. | 623/1.15 |
| 6,443,982 B1 | 9/2002 | Israel et al. | |
| 6,461,381 B2 | 10/2002 | Israel et al. | |
| 6,464,722 B2 | 10/2002 | Israel et al. | |
| 6,508,834 B1 | 1/2003 | Pinchasik et al. | |
| 6,579,314 B1 * | 6/2003 | Lombardi et al. | 623/1.44 |
| 6,589,276 B2 | 7/2003 | Pinchasik et al. | |
| 6,635,084 B2 | 10/2003 | Israel et al. | |
| 6,682,554 B2 | 1/2004 | Von Oepen et al. | |
| 6,875,228 B2 | 4/2005 | Pinchasik et al. | |
| 6,974,475 B1 | 12/2005 | Wall | |
| 2002/0095208 A1 | 7/2002 | Gregorich et al. | |
| 2002/0116044 A1 * | 8/2002 | Cottone et al. | 623/1.2 |

* cited by examiner

STENT HAVING HELICAL ELEMENTS

This application claims the benefit of U.S. Provisional Application No. 60/254,688, filed on Dec. 11, 2000, which is hereby incorporated in its entirety by reference, and is a continuation-in-part of U.S. patent application Ser. No. 09/511,481, filed on Feb. 23, 2000 now U.S. Pat. No. 7,108,714, which is also hereby incorporated in its entirety by reference and which is a continuation of U.S. patent application Ser. No. 09/094,402, filed Jun. 10, 1998 —now U.S. Pat. No. 6,117,165.

BACKGROUND OF THE INVENTION

1. Field of the Invention

The present invention relates to prosthetic stents. In particular, the present invention relates to stents having helical elements and to methods for manufacturing the stents of the present invention.

2. Description of Related Art

Stents are prosthetic devices that are implanted in the lumen of a vessel inside the body to provide support for the vessel's wall. Structural support from stents is particularly important in angioplasty procedures. Typically, stents are implanted within a vessel system to reinforce vessels that are partially occluded, collapsing, weakened, or abnormally dilated. More generally, stents can be used inside any physiological conduit or duct including, for example, arteries, veins, bile ducts, the urinary tract, alimentary tracts, the tracheobronchial tree, a cerebral aqueduct or the genitourinary system. Stents may be used in both humans and animals.

There are typically two types of stents: self expanding stents and balloon expandable stents. Self expanding stents automatically expand once they are released and assume a deployed, expanded state. A balloon expandable stent is expanded using an inflatable balloon catheter. The balloon is inflated to plastically deform the stent. Balloon expandable stents may be implanted by mounting the stent in an unexpanded or crimped state on a balloon segment of a catheter. The catheter, after having the crimped stent placed thereon, is inserted through a puncture in a vessel wall and moved through the vessel until it is positioned in the portion of the vessel that is in need of repair. The stent is then expanded by inflating the balloon catheter against the inside wall of the vessel. Specifically, the stent is plastically deformed by inflating the balloon so that the diameter of the stent is increased and remains at an increased state. In some situations, the vessel in which the stent is implanted may be dilated by the stent itself when the stent is expanded.

The Palmaz-Schatz™ stent, which is disclosed in the *Handbook of Coronary Stents* by Patrick W. Serruys et al. (Martin Dunitz, LTD 1998), is an example of a balloon expandable stent that had been implanted in hundreds of thousands of patients. The Palmaz-Schatz™ stent, like other known stents, has certain limitations. These include, but are not limited to: (i) low stent-to-vessel ratio uniformity, (ii) comparative rigidity of the stent in a crimped as well as deployed state, and (iii) limited flexibility making delivery and placement in narrow vessels difficult. Stent-to-vessel ratio generally refers to the degree that the vessel wall is supported by the stent in its expanded state and preferably should be uniform throughout the length of the stent. Furthermore because the Palmaz-Schatz™ stent consists of one or more bridges that connect a number of consecutively slotted tubes, there are a number of bare areas in the vessel after the expansion of the stent. These shortfalls are common to many stents. Id. at 36.

SUMMARY OF THE INVENTION

The present invention is directed to expandable stents that have relatively uniform stent-to-vessel ratios when expanded and other desirable properties, as well as methods for making these stents. The stents of the present invention comprise a generally cylindrically shaped main body having a plurality of expandable helical segments. The main body is comprised of a plurality of cylindrical main body elements that are joined together by the helical segments. The cylindrical elements have cylindrical axes that are collinear with the cylindrical axis of the main body. The cylindrical elements are formed from a plurality of circumferential elements that are joined together by the expandable helical segments. In some embodiments, the stent may comprise endzones that straddle the main body.

In one embodiment of the present invention, the stent may comprise a first non-helical endzone and a second non-helical endzone that straddle the main body. The main body is generally cylindrically shaped and has a cylindrical axis. A plurality of adjacent main body cylindrical elements are connected together to form the main body of the stent. Each main body cylindrical element may be comprised of a plurality of expandable first and second circumferential elements. In some embodiments, the second circumferential elements have a circumferential dimension less than the circumferential dimension of the first circumferential elements. In yet other embodiments, the first and second circumferential elements have the same circumferential dimensions and are substantially identical except that, with respect to the cylindrical axis of the stent, they are oriented differently. Each second circumferential segment in each main body cylindrical element is connected to two first circumferential segments. In addition, each second circumferential segment in each main body cylindrical element is connected to a second circumferential segment in an adjoining main body cylindrical element thereby forming a plurality of helixes in the main body of the stent.

In one embodiment, the main body may be comprised of a plurality of first helical segments each having a substantially identical first pitch and a plurality of second helical segments, each having a substantially identical second pitch. The first and second pitches are generally different. In at least one embodiment, the second pitch is twice that of the first, and at least one first helical segment crosses one of the second helical segments.

The stents of the present invention may be manufactured from a tubular member by removing material from the tube to form a first endzone region, a second endzone region, and a middle region. By removing material from the middle region a plurality of parallel helical segments will remain and a plurality of circumferential segments will remain connecting the helical segments. Alternatively, the stent may be formed from a tube by removing material such that at least two sets of helical segments remain with each set having a different pitch.

DETAILED DESCRIPTION OF THE INVENTION

Figure 1:
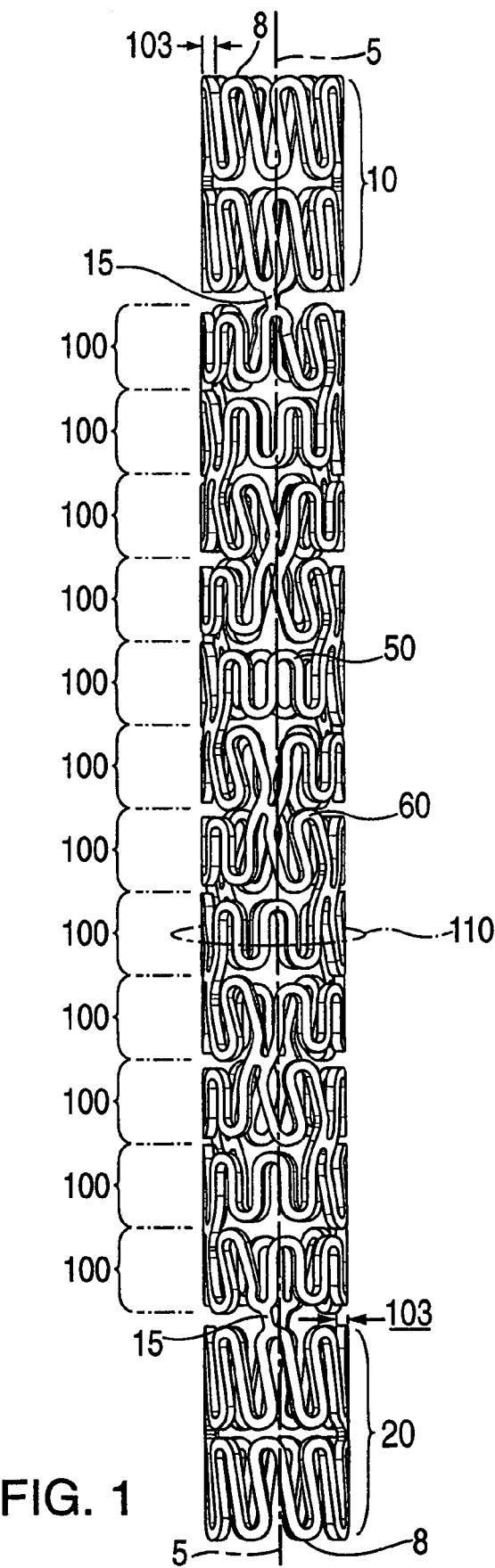
FIG. 1 is a three dimensional view of one embodiment of a stent according to the present invention in its unexpanded state.
Figure 2:
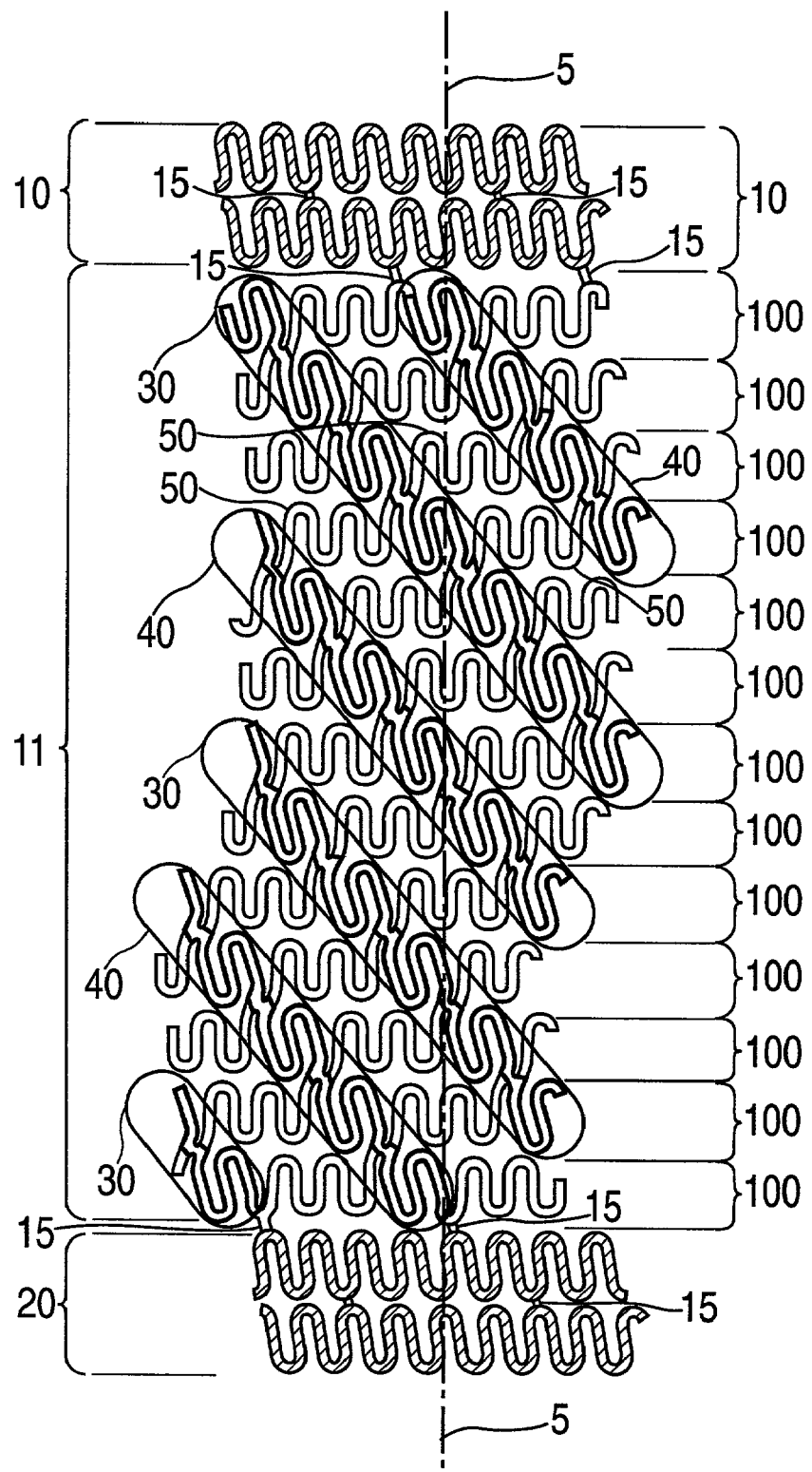
FIG. 2 is planar view of a flattened portion of the circumference of the stent in FIG. 1.

The present invention is directed to an expandable stent, as well as a method of manufacturing the stent. In one embodiment, as is shown in FIGS. 1 and 2, the stent comprises a generally cylindrical shaped main body section 11 having a cylindrical axis 5 and a wall thickness 103. The wall thickness 103 may optionally be uniform throughout the stent. The main body section 11 is comprised of a plurality of helical segments 30 and 40 and a plurality of main body cylindrical elements 100, each having cylindrical axes (not shown) that are collinear with the main body cylindrical axis 5. The main body cylindrical elements 100 are each comprised of circumferential elements 50 that are joined together by the helical segments 30 and 40 to form individual cylinders 100.

The stent may also have a first endzone 10 and a second endzone 20 that straddle the body section 11. In some embodiments, such as the one shown in FIG. 1, the endzones 10 and 20 may advantageously provide the stent with square outer edges 8. The stent may be manufactured from stainless steel, or other suitable materials. In most embodiments, it is desirable that the material, or a portion of the material, be radiopaque and that the various segments that form the stent be contiguous. Although, in some embodiments, the various segments that make up the stent can be distinct elements that are joined together.

The main body 11, shown in FIGS. 1 and 2, may be formed in numerous ways. For example, the body 11 may contain two or more first helical segment 30 and 40 that are generally parallel to each other. In some embodiments they may be opposite each other by 180.° In general, the first helical segments 30 and 40 will be spaced equidistant along the circumference 110 of the main body 11. The first helical segments 30 and 40 are joined by a plurality of circumferential segments 50 to form a plurality of main body cylindrical elements 100, which may be only generally cylindrically shaped. In one embodiment, the circumferential segments 50 make up a majority of the circumference 110 of each cylindrical element 100. In addition to joining the circumferential elements 50 to form cylindrical elements 100, the helical segments 30 and 40 connect each cylindrical element 100 to an adjacent cylindrical element 100 to form the main body 11.

Figure 3:
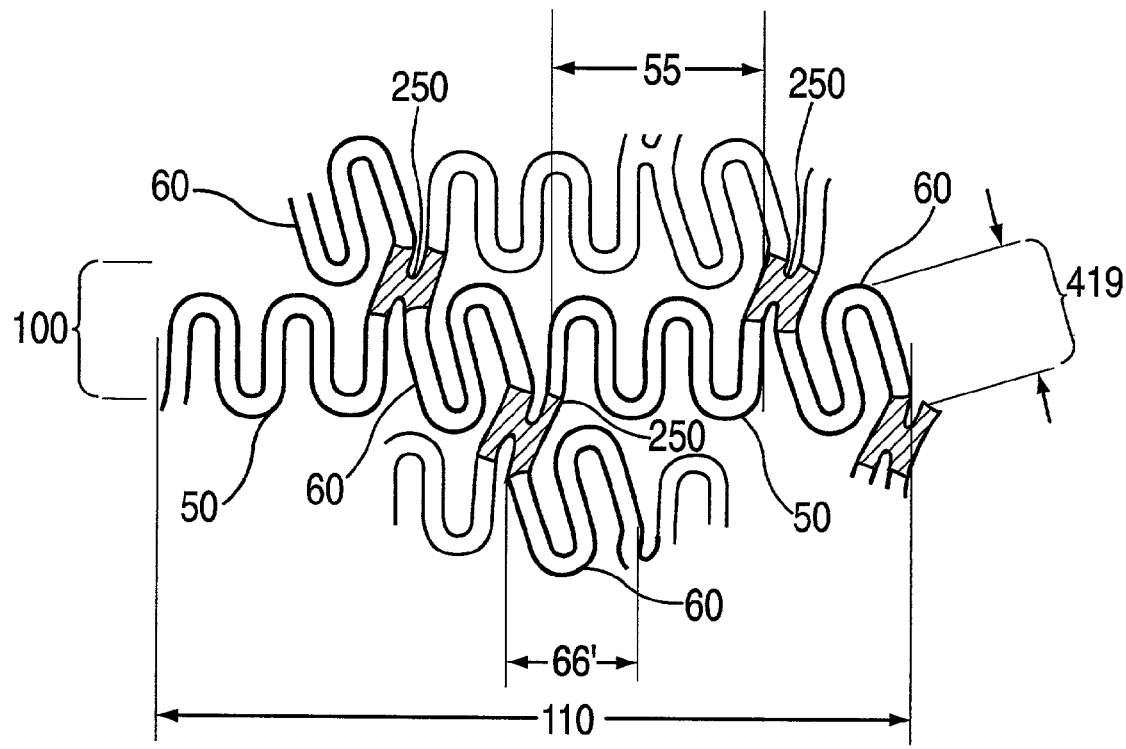
FIG. 3 is an enlarged portion of FIG. 2.
Figure 5:
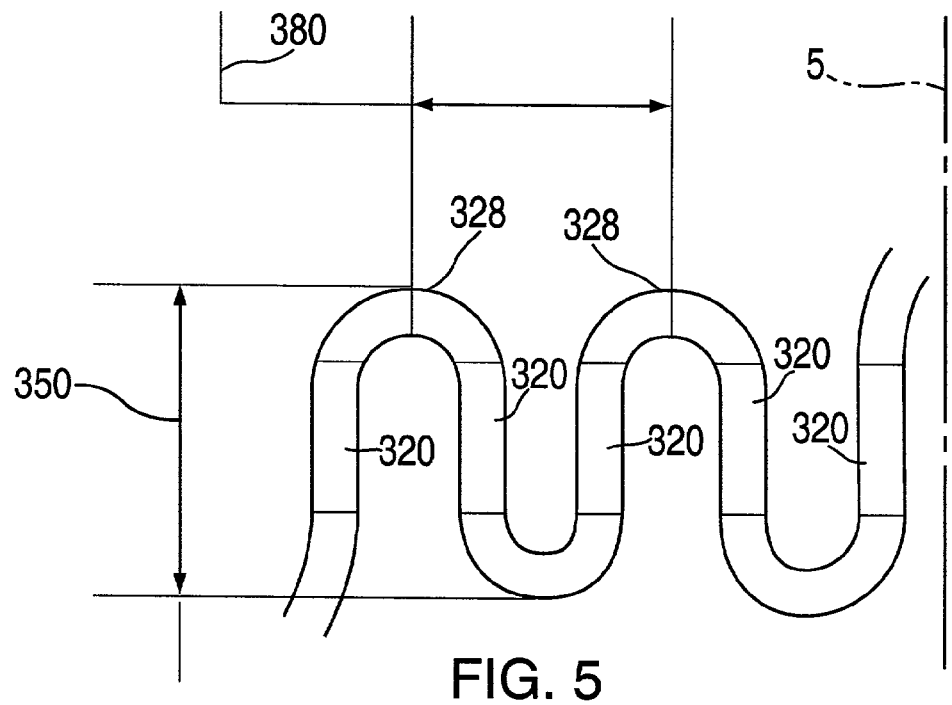
FIG. 5 is an enlarged view of a portion of FIG. 4 showing a first circumferential element of the stent.

As is shown in FIGS. 2 and 3, the body of the stent 11 may comprise a plurality of main body cylindrical elements 100 formed from first circumferential segments 50 that are joined with second circumferential segments 60. The second circumferential segments 60 of each cylindrical element 100 may be joined with second circumferential segments 60 of adjacent cylindrical elements 100 to form a plurality of first helical segments 30 and 40 in the main body 11. (See FIG. 2). Each first circumferential segment 50 may have a circumferential dimension 55 and each second circumferential segments 60 may have a circumferential dimension 66' (See FIG. 3). In some embodiments, it may be desirable for the circumferential dimension 55 of the first expandable element 50 to be larger than the circumferential dimension 66' of the second expandable element 60.

The first circumferential segment 50 may be an expandable segment formed from plurality of segments joined together to form a pattern. The pattern, such as the one shown in the FIGS. 1-3, may be a repeating pattern that resembles a square wave form having curved peaks and valleys. Other patterns, both repeating and non-repeating, may be used. For example, and without limitation, the first circumferential segments 50 may resemble a triangle wave form, a sinusoidal wave form, other repetitious patterns, or any pattern that enables the segment to expand when a radial force is exerted on the stent from the inside or collapse radially when an external crimping force is applied.

Figure 4:
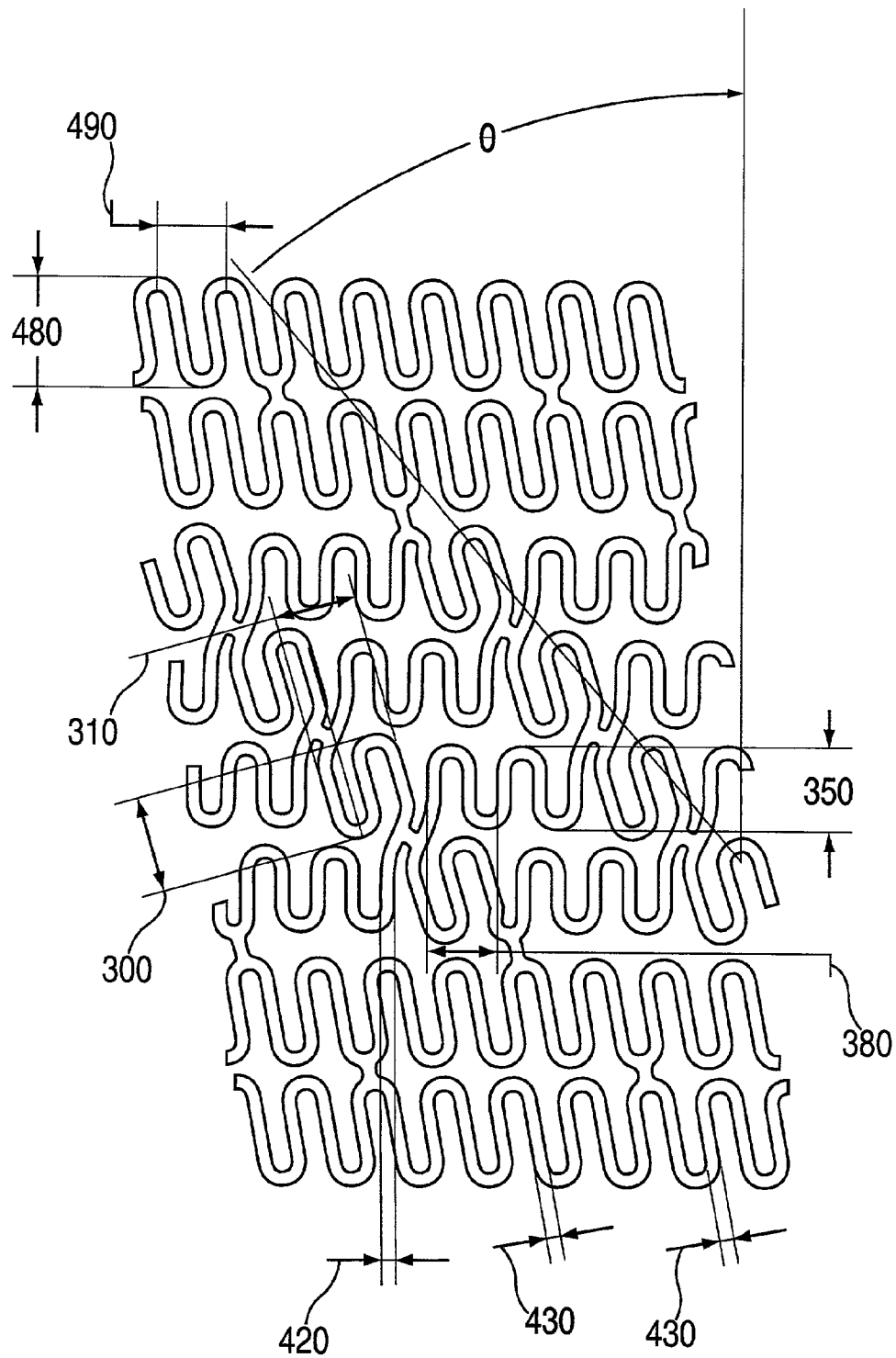
FIG. 4 is another planar view of a flattened portion of the circumference of a stent according to the present invention in its unexpanded state.

The first circumferential elements 50 may have a filament width 420 (see FIG. 4). In one embodiment, the filament width may vary between 0.002 inches and 0.007 inches, but is preferably about 0.0050 inches. Other filament widths may be used depending on the parameters of the stent.

In the embodiment shown in FIGS. 1-5, the first circumferential elements 50 comprise linear portions 320 and curved portions 328 that join the linear portions 320 together to form a repeating pattern. In some, but not all, embodiments, the linear portion 320 may be parallel to the cylindrical axis of the stent. In other embodiments, the linear portion 320 lies at an angle of between 0-45 degrees with respect to the cylindrical axis. The first circumferential segment 50 has an amplitude 350 and a period 380. In one embodiment the amplitude may range from 0.5 mm to 2.0 mm and the period may range from 0.5 mm to 2.0 mm. In some embodiments, the amplitude is less than the period. Other amplitudes and periods may be used depending on the overall stent design and performance constraints.

Figure 6:
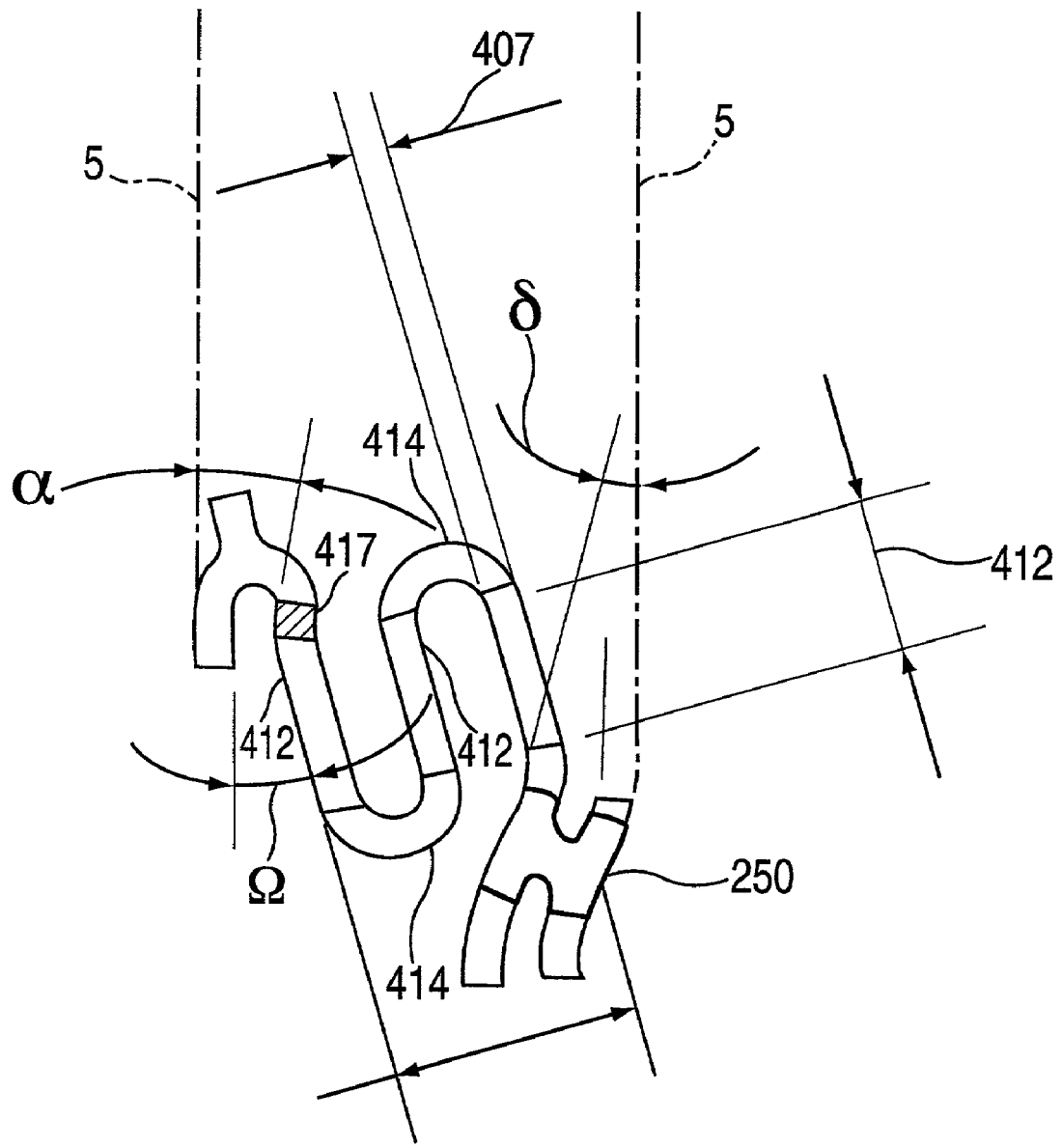
FIG. 6 is an enlarged view of a portion of FIG. 4 showing a second circumferential element of the stent.

The second circumferential element 60, which may be joined together in a helical pattern to form one or more helical segments 30 or 40, may also take numerous forms, in addition to the form shown in FIG. 6. In the embodiment shown in FIG. 6, the second circumferential element 60 comprises linear portions 412 and curved portions 414 having a filament width 407, and resembles generally an S-shaped structure. In addition, the second element circumferential segment 60 may have an angled portion 417 attached to the linear portion 412 at an end opposite that of the curved portion 414. The angled portion may be oriented to form an angle α relative to the cylindrical axis of the stent 5 in the range of 0-45 degrees. In at least one embodiment, the preferable angle α is about 10 degrees. In some embodiments, the linear portions 412 of the second circumferential element 60 lies at an angle Ω relative to the cylindrical axis of the stent, wherein Ω preferably ranges from 0 to 45 degrees. When viewed in a planar fashion as in FIG. 2, the linear portions 412 may, in some embodiments, form an angle Ω, relative to the cylindrical axis of the stent. In some embodiments, Ω may be approximately equal to the helical angle of the first helical segments 30 and 40. In one embodiment, the second circumferential elements 60 may have an amplitude 300 (see FIGS. 3, 4, and 6) ranging from 0.5 mm to 2.0 mm and a period 310 ranging from 0.5 mm to 2.0 mm. Other ranges may be used depending on the particular stent size and design being employed. In one embodiment, the preferred period is about 0.82 mm and the preferred length of the linear portion 412 is about 0.5 mm and the amplitude 300 is about 0.38 mm. The amplitude of the second circumferential element 60 may be greater than, equal to, or less than the amplitude of the first circumferential element 50. In one embodiment, the circumferential contributions of the first circumferential elements 50 to the overall circumference of the main body 11 is greater than the circumferential contribution of the second circumferential element 60, in terms of either circumferential length or circumferential cylindrical surface area. In one embodiment, the stent may have an overall outer surface area of about 0.029 square inches.

Figure 7:
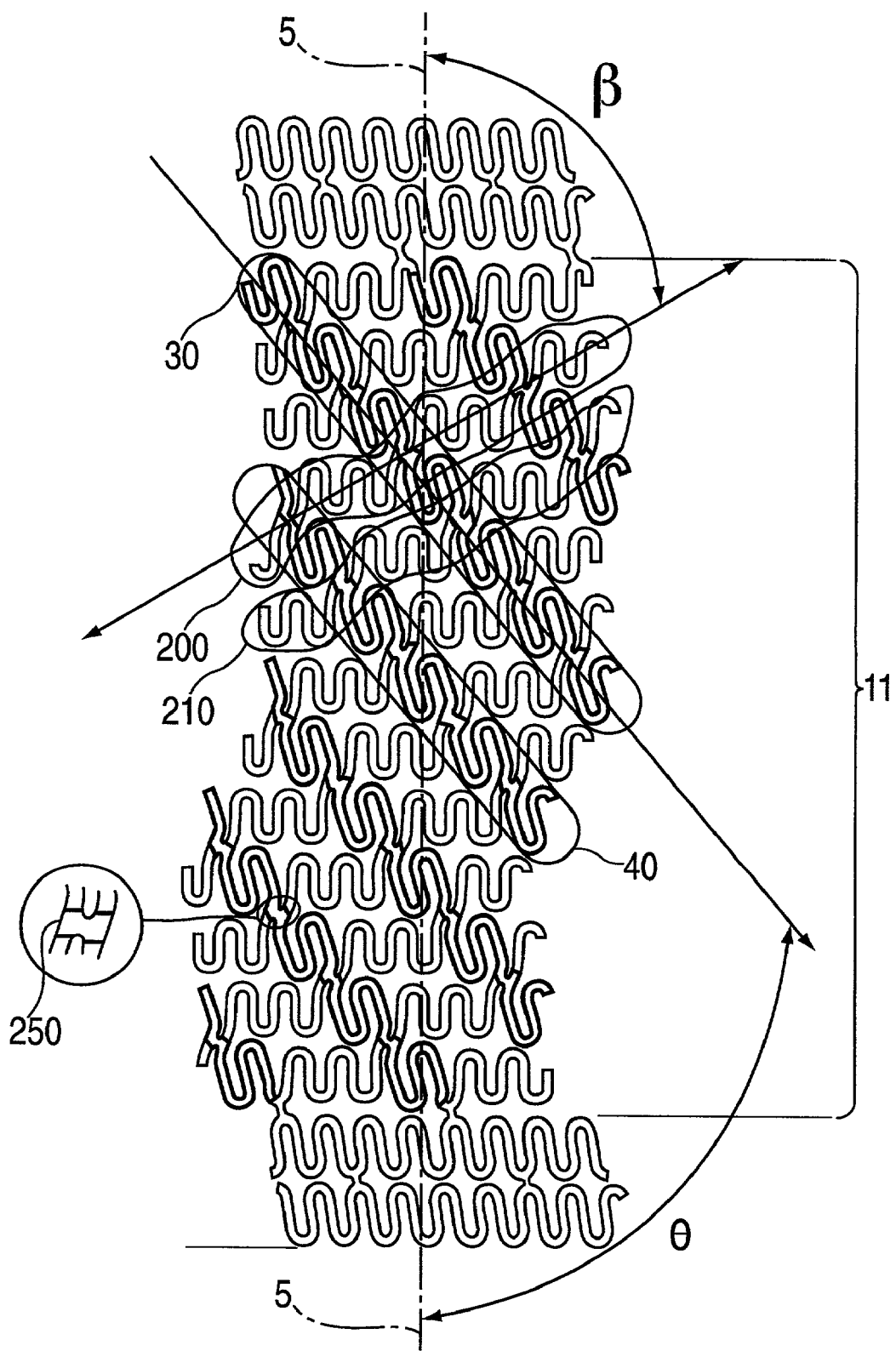
FIG. 7 is a planar view of a flattened portion of the stent in FIG. 1 showing a plurality of sets of helical segments propagating through the stent's body.

As is shown in FIG. 7, the stent may have a main body 11 comprised of two or more first helical segments 30 and 40, as well as two or more second helical segments 200 and 210. The first and second helical segments 30, 40 and 200, 210, respectively, are joined together to form a generally cylindrically shaped body 11. In some, but not all embodiments, the first and second helical segments may share a common connecting element 250. In some embodiments, the common connecting element 250 may be H-shaped and the two generally parallel linear portions of the H-shaped connecting segment 250 may form an angle δ relative to the axis 5. (See FIG. 6). δ may, in one embodiment, be about 14 degrees. As is shown in FIG. 7, the first helical segments 30 and 40 and second helical segments 200 and 210 may have different pitches, i.e. number of spirals per unit length, which results in the first and second helical segments as having different helical angles (θ and β, respectively) i.e. the angle of the helical segment relative to the cylindrical axis 5 of the stent. In one embodiment, the second helical segments 200 and 210 have a pitch approximately twice that of the first helical segments. In one embodiment θ may vary from 0 to 45 degrees and is preferably about 40 degrees and β is preferably about twice θ. In other embodiments the angle θ may range from 0 to 90 degrees.to the circumference 110 of each cylindrical element 100.

As is shown in FIGS. 2, 3, 4, and 6, the helical segments 30, 40 are circumferentially expandable (i.e. they expand along the circumference of the stent) and may be formed from a plurality of circumferential elements 60 that in turn are made up of linear 412 and/or curved 414 segments (see FIG. 6) that each have a filament width 407 (see FIG. 6) that is less than the circumferential dimension 66 of the circumferential element 60 (see FIG. 3). In some embodiments, each helical segment 30 or 40 will make a total contribution to the circumference of each cylindrical element 100 that is greater than the filament width 407. The circumferential contribution of each helical segment 30 or 40 to the overall circumference of the stent (110 in FIG. 1 or 105 in FIG. 11) may be greater than the circumferential contribution of the filament widths 407 of the segments (e.g. 412 and 414) making up the circumferential elements 60 that in turn make up the helical segments. (I.e., In some embodiments the circumferential contribution of the helical segments 30 and 40 to the circumference 110 of each cylindrical element 100 is more than just a function of the filament width 407, e.g., it may be a function of the geometry of the element 60.) For the embodiment shown in FIGS. 1 and 11, this is the case when the stent is in both the unexpanded and expanded state. The geometry of the helical segments 30 and 40 are a factor in determining their expandability.

Likewise, the helical segments 200, 210 are circumferentially expandable and may be comprised of other circumferential elements 50 that are in turn comprised of linear 320 and/or curved segments 328 (see FIGS. 3 and 5) that have a filament width 420 (see FIG. 4). The contribution of the helical segments 200, 210 to the overall circumferential dimension 110 of each cylindrical element 100 is greater than just the contribution of the filament widths 420 of the individual segments 320 and 328 that make up the elements 50 that in turn make up the helical segments 200, 210. The geometry of the elements 50 making up the helical segments 200, 210 may be a more important factor in determining the circumferential contribution of the helical segments 200 and 210 to the overall stent circumference than the filament width 420. Thus, in one embodiment of the present invention, the circumference of the stent 110 in its unexpanded state and the circumference 105 when the stent is expanded are primarily functions of the geometry of the elements 50 and 60 that make up the helical segments 30, 40 and 200, 210, respectively.

Figure 8:
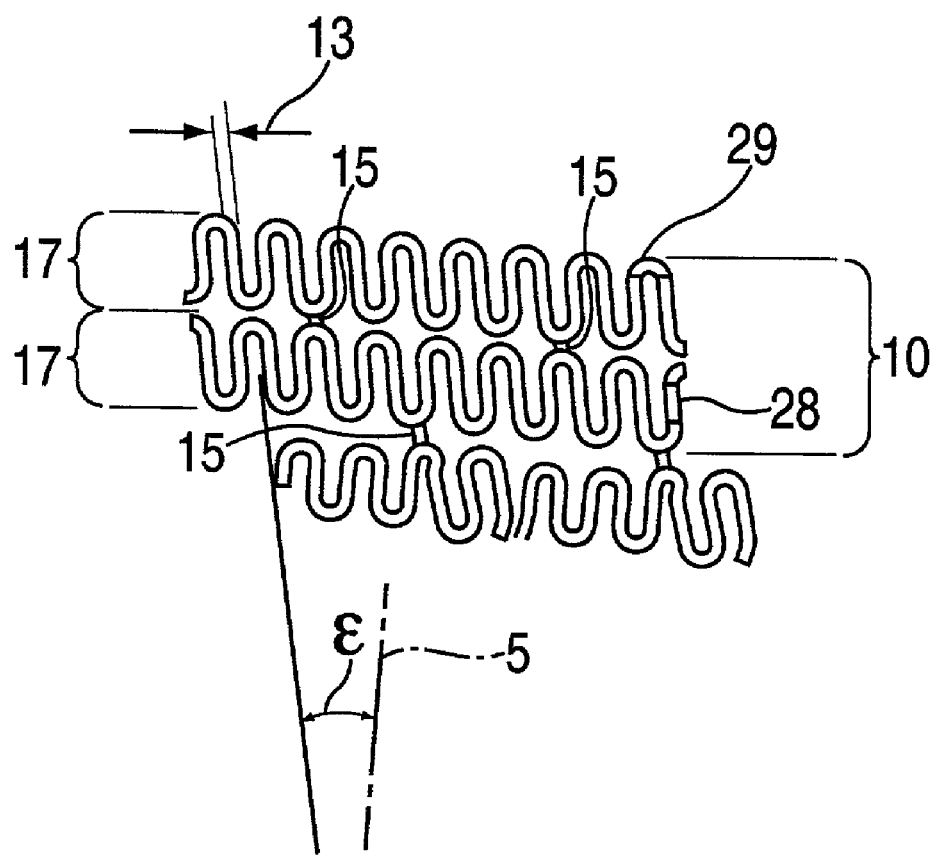
FIG. 8 is a planar view of a flattened endzone that may be employed in a stent of the present invention.
Figure 9:
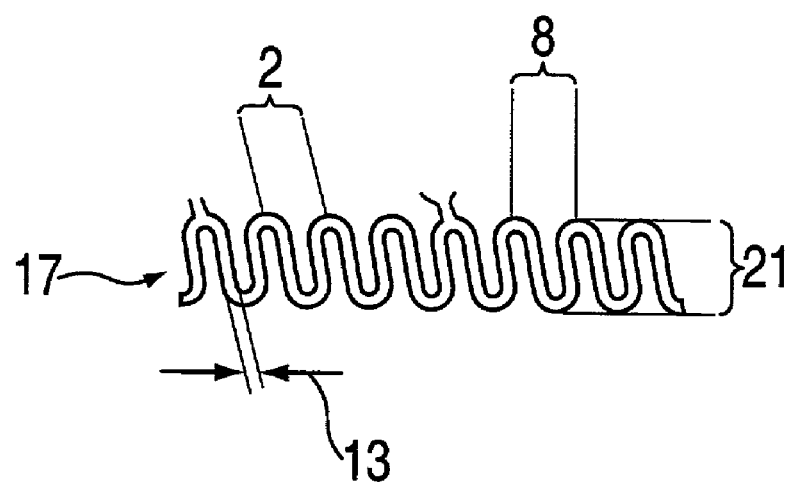
FIG. 9 is a planar view of a flattened portion of part of the endzone shown in FIG. 8.
Figure 10:
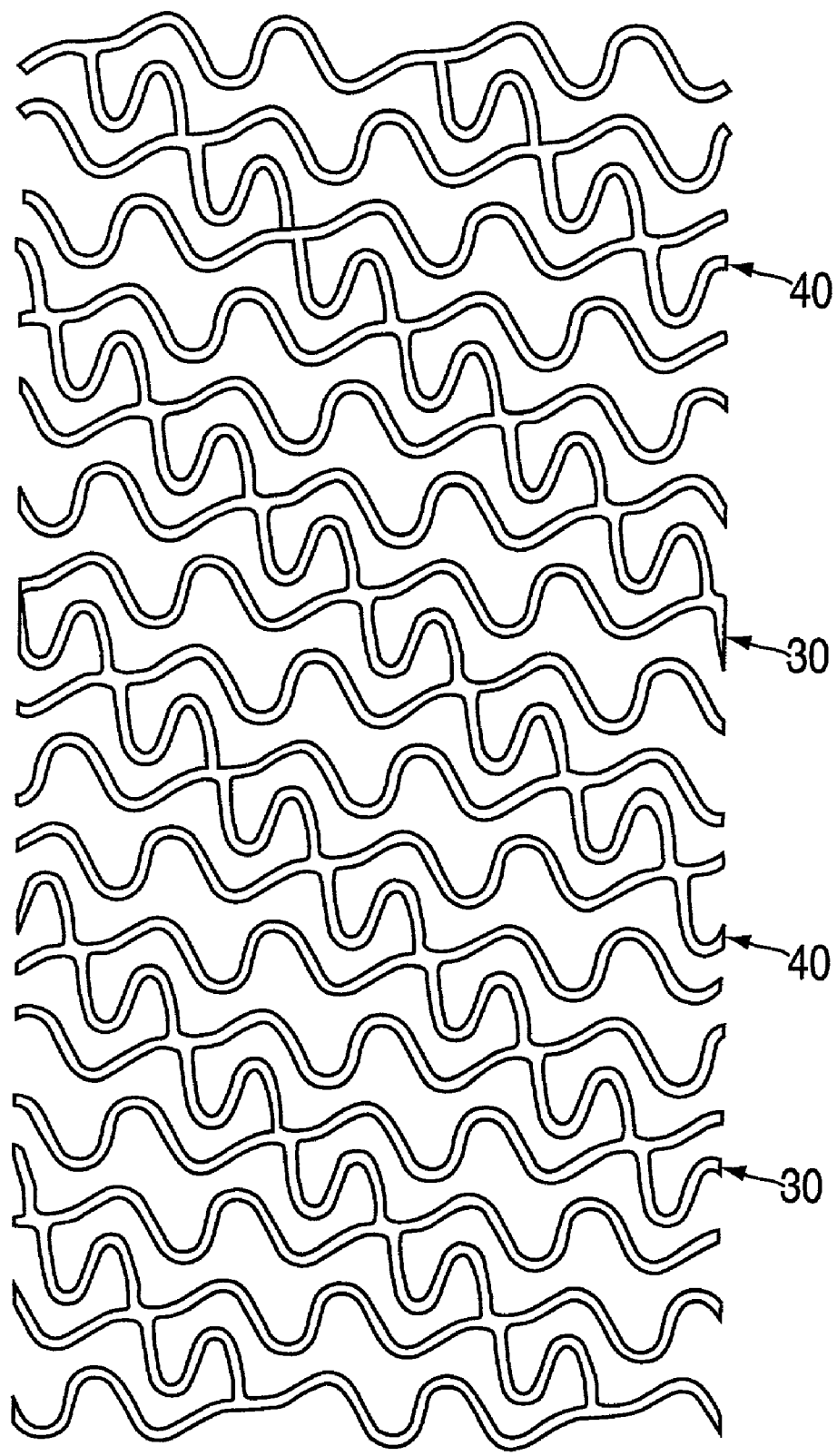
FIG. 10 is a planar view of a flattened portion of an expandable stent according to the present invention, after the stent has been deployed in a lumen.

Some, but not all embodiments, of the present invention may employ endzones 10 and 20. (See FIGS. 1, 2, and 11). Stents that employ endzones will generally have two endzone regions straddling a central zone in the middle of the stent. The stents may also have a transition region between the endzone and the central zone. The transition region serves to help smoothly transition between the expanded middle region and portions of the end of the stent that remain unexpanded after the stent is implanted. The size and characteristics of the transition region are a function of the material and geometry of the stent. For example, the transition range properties vary as a function of, among other things, the helical angle of the first helical segments, the number of curved segments located in the endzones, and the angle ε of the linear portions of the segments forming the endzones. (See e.g. FIG. 8).

The endzones 10 and 20 may take numerous forms. In some embodiments, the endzones may be comprised of one or more rings 17. (See FIG. 8). The rings 17 may be generally cylindrically shaped, and in some embodiments, right cylindrically shaped. In one embodiment, the rings are formed from linear segments 28 joined together by curved segments 29 to form a pattern. The pattern, which is preferably—but not necessarily—a repeating pattern may take numerous forms, including the one shown. The endzones 10 and 20 may be comprised of a plurality of rings 17 attached together. Struts 15 may be used to attach the rings together to form the endzone and to attach the endzone to the main body 11. The struts, in some embodiments, act as cantilever springs and there stiffness, which is a function of their width and thickness, may define bending properties of the stent along its cylindrical axis 5.

In the embodiment shown in FIGS. 1, 7, 8, and 9, which is exemplary only, the linear segments 28 in the endzone 10, are oriented at an angle ε relative to the cylindrical axis of the stent. In one embodiment, the angle ε is greater than 0 degrees. In another embodiment, ε may range from 0 to 45 degrees and in still another embodiment is preferably about 10 degrees. The segments of the endzone may have a filament width 13 of between 0.002 and 0.007 inches. In one embodiment, the repeating pattern of the endzone has a period 2 of about 0.027 inches and an amplitude 21 of about 0.043 inches. Other values may be used. As is shown in FIG. 1, the struts 15, which are but one way to attach the endzones 10 and 20 to the main body 11, may, in one embodiment have a width of between 0.002 inches and 0.08 inches and preferably the width does not exceed the wall thickness, which typically—but not necessarily ranges from about 0.002 to 0.008 inches.

Figure 11:
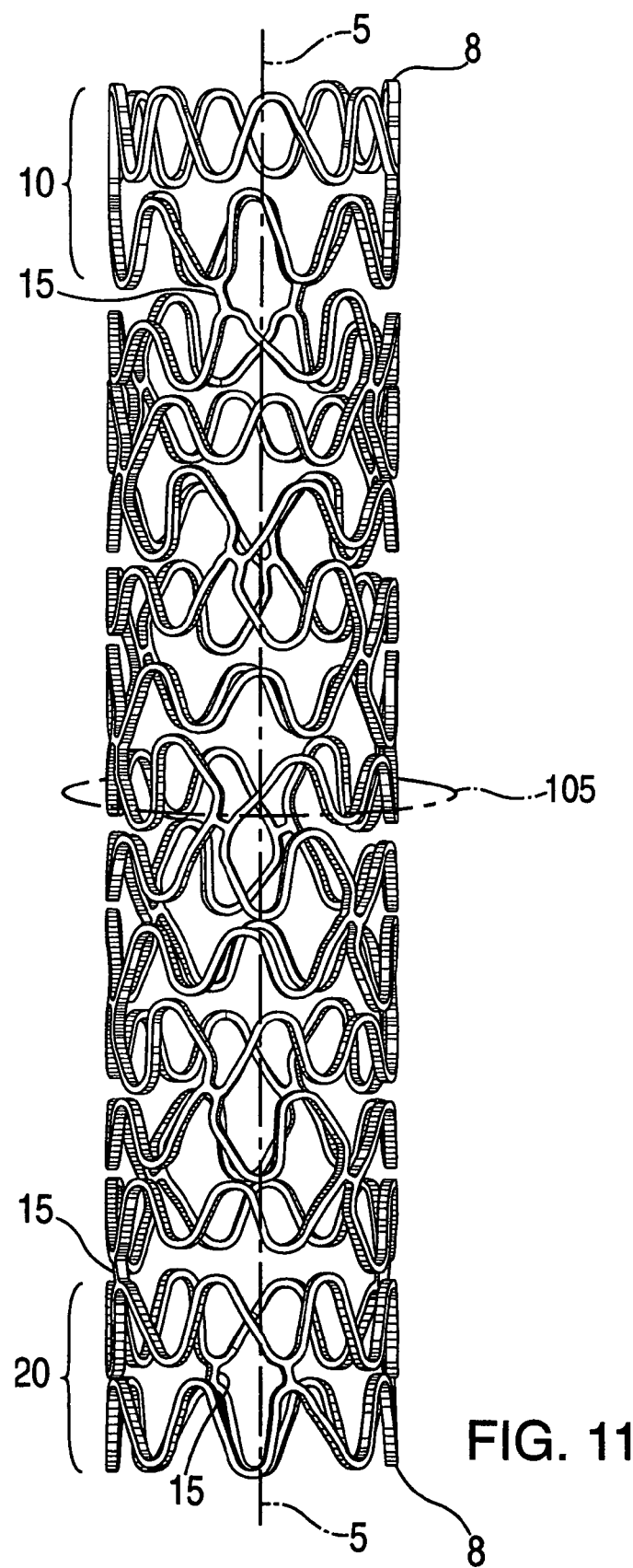
FIG. 11 is three dimensional view of an alternative embodiment of the present invention.
Figure 12:
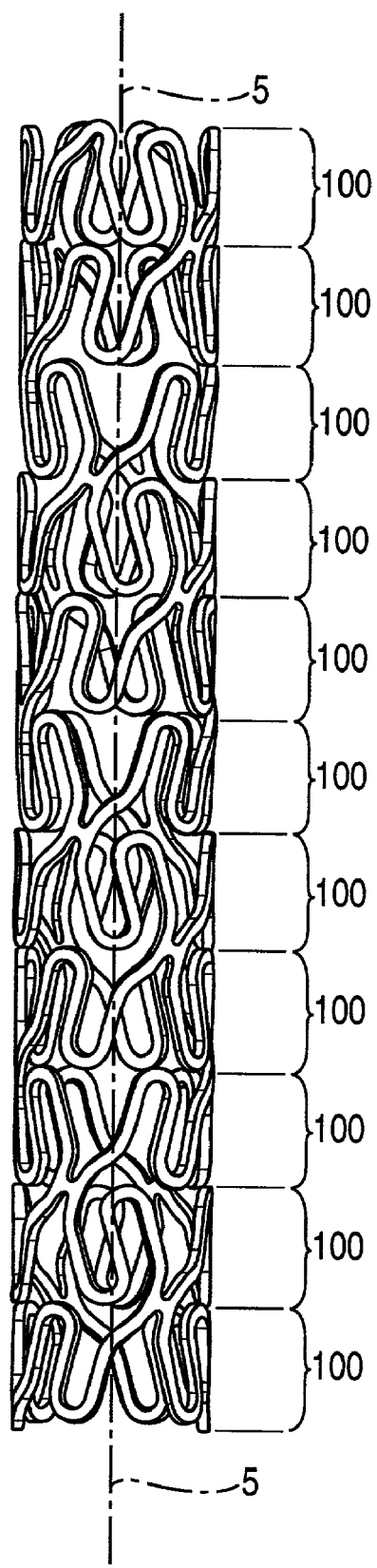
FIG. 12 is a three dimensional view of an another stent according to the present invention.
Figure 13:
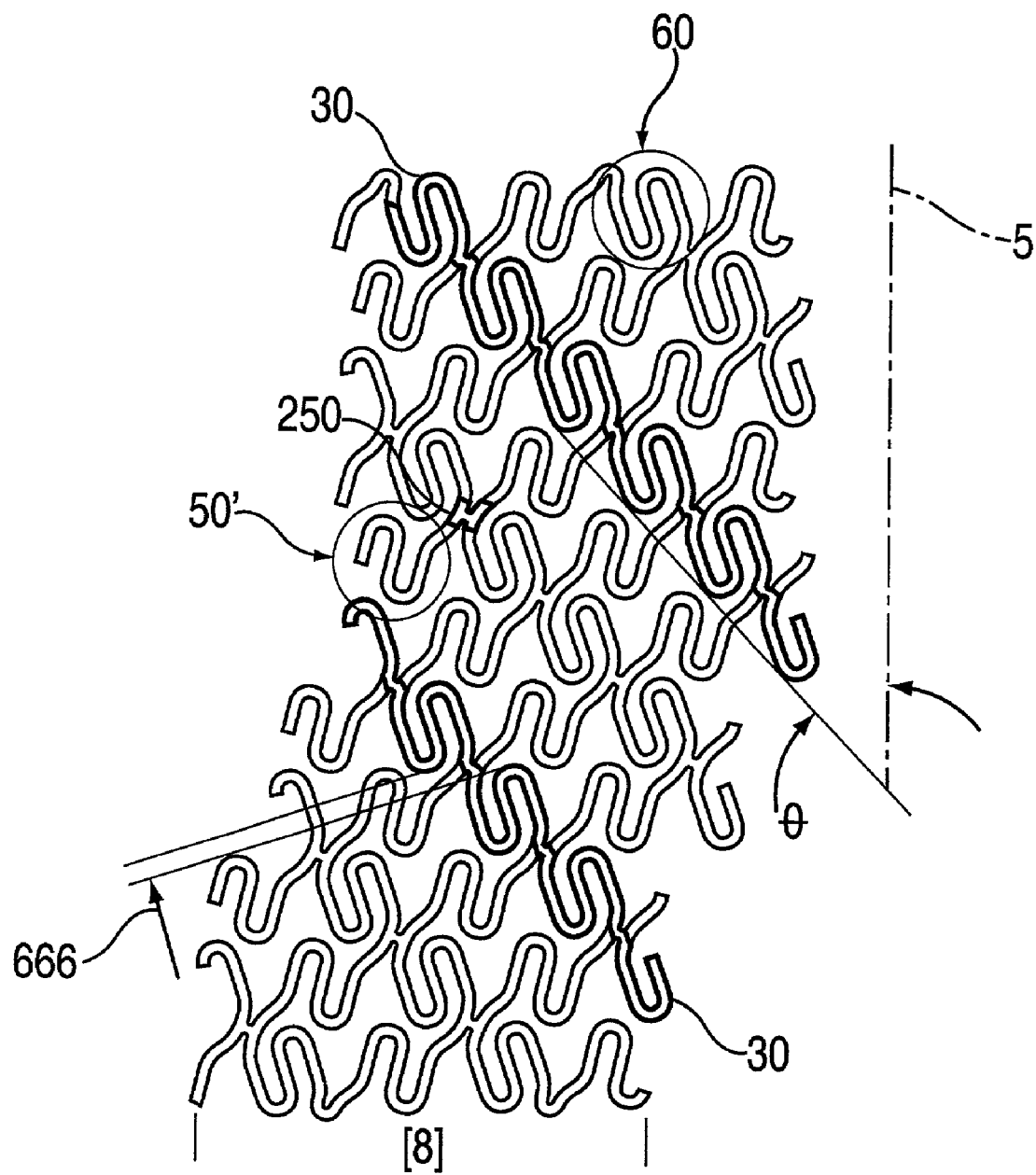
FIG. 13 is a planar view of the stent shown in 12.
Figure 14:
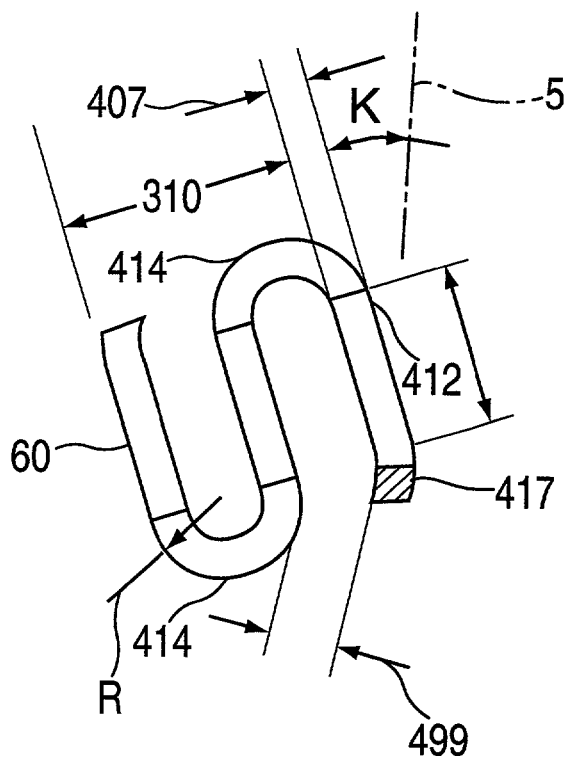
FIG. 14 is a detailed view of a portion of FIG. 13.

The stent of the present invention may, after insertion into a vessel, be expanded such that it plastically deforms from the unexpanded state to an expanded state having a diameter increase of about 400 to 500%, which results in a larger circumference 105. (See FIG. 11). FIG. 11 depicts the stent shown in FIG. 1 in an expanded state. Upon expansion the stent's outer diameter in one particular embodiment increases from 1.0 mm to 3.00 mm and maintains a stent-to-vessel ratio in the expanded state that is greater than on average 16%.

Figure 15:
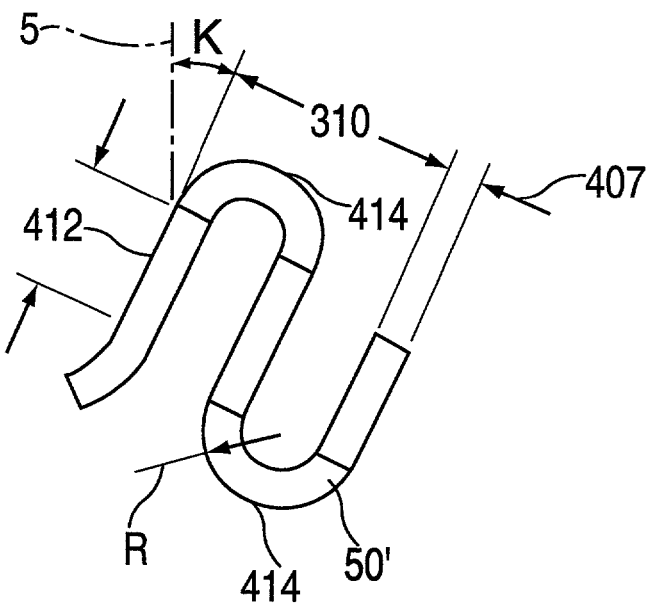
FIG. 15 is a detailed view of another portion of FIG. 13.

While endzones 10 and 20 may be used to provide square edge, not all stents according to the present invention require endzones. FIGS. 12-15 depict an endzoneless stent. Like the stent shown in FIGS. 19, the stent of FIGS. 12-15 comprises a plurality of adjacent cylindrical elements 100. The cylindrical elements 100 are formed from a plurality of first circumferential elements 50' and second circumferential elements 60. The first circumferential elements 50' of the stent in FIGS. 12-15 are substantially identical to the second circumferential element 60 except that they are rotated to have a different orientation. The circumferential elements may be generally S-shaped having a linear portion 412, a curved portion 414 having a radius R, and an angled portion 417. R may vary widely depending on overall stent characteristics and in one embodiment varies between 0.001 and 0.02 inches and is preferably about 0.0083 inches. The angled portion 417 is spaced a distance 499 from the linear portion. In one particular embodiment, the distance 499 may vary from 0.002 to 0.020 inches and is preferably about 0.007 inches. The filament width 407 of the elements may, in one embodiment, be about 0.13 mm. The circumferential elements depicted in FIG. 14 and the expansion elements depicted in FIG. 15 are positioned about the cylindrical axis 5 as defined by angle K and may be generally S-shaped having a linear portion 412, a curved portion 414 having a radius R, and an angled portion 417. The angle K may vary widely depending on overall stent characteristics and range of radial compression or expansion about the axis 5.

Adjacent cylindrical elements 100 are joined together by connecting first circumferential elements 50' in each cylindrical element 100 with first circumferential elements 50' in an adjacent cylindrical element 100, such that the first circumferential elements 50' in adjacent cylindrical elements 100 form helixes through the stent and such that second circumferential elements form helixes through the stent having an angle θ relative to the axis 5. In some embodiments, a connecting segment 250 (see FIG. 7) is used to connect first circumferential elements in adjacent cylindrical elements 100 and to connect second circumferential elements 60 in adjacent cylindrical elements 100. In addition, the connecting segment, connects first circumferential elements 50' in each cylindrical element 100 with two second circumferential elements 60 in each cylindrical element 100. In one embodiment, the individual cylindrical elements 100 are adjacent to each other and are located a distance 666 apart. In one embodiment, the preferred may range between 0.002 and 0.020 inches, and is preferably about 0.009 inches.

The above description of the stent of the present invention is illustrative and not exhaustive. Various modifications may be made to the stent to change its overall characteristics without deviating from the scope and spirit of the invention as defined by the claims. For example and without limitation, the increasing the length of the linear segments and or increasing the arc of the second circumferential elements 60 will decrease the amount of radial force required to expand each circular section and will increase flexibility. Increasing the angle Ω of the second circumferential element 60 will: (i) increase the amount of radial force required for expansion, (ii) increase surface area, and (iii) decrease flexibility. Likewise, various modifications may be made to the struts 15. (See FIG. 2). Increasing strut width and wall thickness will: (i) increase surface area, (ii) increase radial strength, (iii) increase pressure required to expand the stent radially, (iv) decrease flexibility, and, in the case of increased wall thickness, (v) increase radiopacity.

The stent of the present invention may be manufactured in numerous ways. The stent may be formed from a metallic tube by removing various portions of the tube's wall to form the patterns described herein. The resulting stent will thus be formed from a single contiguous piece of material, eliminating the need for connecting various segments together. Material from the tube wall may be removed using various techniques including laser (YAG laser for example), electrical discharge, chemical etching, metal cutting, a combination of these techniques, or other well known techniques. See e.g. U.S. Pat. Nos. 5,879,381 to Moriuchi et al. and 6,117,165 to Becker, which are hereby incorporated in their entirety by reference. Forming stents in this manner allows for creation of a substantially stress-free structure where the helical segments are integral with the circumferential elements. In one embodiment, the tube from which the stent is formed may have an internal diameter of about 3.0 mm, a wall thickness of about 1.0 mm and a length of about 30 mm. Tubes having other dimensions may be used. In particular, the length may be adapted to that of the diseased part of the lumen in which the stent is to be placed. This may avoid using separate stents to cover the total diseased area.

Those skilled in the art will recognize that the stent and manufacturing method described above are illustrative and not exhaustive of the present invention and that modifications and variations may be made without deviating from the scope and spirit of the invention as defined by the following claims.

We claim:

1. An expandable stent comprising a main body, wherein, when the stent is unexpanded, the main body comprises:
    a plurality of expandable helical segments that comprise (a) expandable circumferential segments each having a single substantially S-shaped portion and (b) substantially H-shaped connecting segments; and
    a plurality of main body cylindrical elements having collinear cylindrical axes, the main body cylindrical elements being adjacent to one another and being attached to one another by the connecting-segment portions of the helical segments, each main body cylindrical element having
        a circumference that is substantially identical to that of an adjacent cylindrical element and comprising
        a plurality of circumferential segments joined together by the connecting-segment portions of the helical segments, thereby forming the cylindrical element, and the plurality of circumferential segments comprising a majority of the circumference of each cylindrical element.

2. The stent Of claim 1, wherein the circumferential segments are comprised of a plurality of segments joined together to form a repeating pattern.

3. The stent of claim 1, wherein the repeating pattern comprises a square wave form having curved peaks and valleys.

4. The stent of claim 1, further comprising: a first and second endzone, wherein the first and second endzones straddle the main body of the stent.

5. The stent of claim 4, further comprising a plurality of struts connecting each endzone to the main body.

6. The stent of claim 5, wherein the endzones are each comprised of a plurality of rings.

7. The stent of claim 6, wherein the rings in each endzone are joined together by a plurality of struts.

8. The stent of claim 7, wherein the rings are comprised of a plurality of alternating linear and curved segments.

9. The stent of claim 8, wherein the linear segments form an angle greater than 0° relative to the cylindrical axis of the cylindrical elements.

10. An expandable stent comprising:
a first non-helical endzone;
a second non-helical endzone;
a generally cylindrically shaped main body having a cylindrical axis, the main body located between the first and second endzones and comprising:
a plurality of adjacent cylindrical main body elements having cylindrical axes collinear with the main body cylindrical axis, the adjacent cylindrical main body elements connected together and comprising:
a plurality of first expandable circumferential segments having a circumferential dimension; and
a plurality of second expandable circumferential segments having a circumferential dimension that is less than the first expandable segment circumferential dimension, each of the second expandable segments connected to two first expandable segments via substantially H-shaped connecting segments; and
wherein the cylindrical main body elements are joined by connecting together, via substantially H-shaped connecting segments, second expandable circumferential segments of adjacent cylindrical main body elements in helical patterns, thereby forming a plurality of generally parallel helixes in the main body.

11. The stent of claim 10, wherein at least a portion of the stent is radiopaque.

12. The stent of claim 10, wherein each of the endzones is attached to the main body with a plurality of struts.

13. The stent of claim 10, wherein the stent is manufactured from a contiguous piece of material.

14. The stent of claim 10, further comprising two helical segments in the main body, wherein the helical segments are 180° apart.

15. The stent of claim 10 wherein each endzone comprises a ring formed from a plurality of contiguous segments.

16. The stent of claim 15, wherein the contiguous segments comprise linear and curved segments and wherein the linear and curved segments are joined together to form a repeating pattern.

17. The stent of claim 16, wherein the first expandable circumferential element comprises a plurality of linear and curved segments joined together to form a repeating pattern that resembles generally a square wave form having curved peaks and valleys.

18. The stent of claim 17, wherein the second expandable element comprises a plurality of linear and curved segments joined together and wherein the linear segments form an angle relative to the cylindrical axis of the stent that is approximately equal to the helical angle of at least one of the helixes in the main body.

19. An expandable stent that, when in an unexpanded state, comprises:
a cylindrical axis,
a cylindrical main body about the cylindrical axis, the main body comprising:
a plurality of main body cylindrical elements having collinear cylindrical axes, the main body cylindrical elements being adjacent to one another and connected to one another by helical segments comprising expandable circumferential segments and substantially H-shaped connecting segments,
wherein the helical segments comprise
a plurality of first expandable helical segments having a first pitch and a plurality of second expandable helical segments having a second pitch that differs in value from the first pitch, and wherein the first helical segments cross the second helical segments and the first and second helical segments are attached to each other via substantially H-shaped connecting segments.

20. The stent of claim 19, wherein the second pitch has a value that is approximately twice that of the first pitch.

21. The stent of claim 19, further comprising a plurality of generally cylindrical shaped endzones having cylindrical axes that are collinear with the main body cylindrical axis.

22. The stent of claim 21, wherein the endzones have square outer edges.

23. The stent of claim 20, wherein the first helical segments are comprised of a plurality of circumferential segments joined together to form a helix.

24. The stent of claim 23, wherein the circumferential segments comprise a plurality of linear and curved segments joined together.

25. The stent of claim 24, wherein the linear segments lie at an angle between 0-45 degrees with respect to the cylindrical axis of the stent.

26. The stent of claim 23, wherein the second helical segments are comprised of a plurality of second circumferential elements joined together to form a second helix.

27. The stent of claim 23, wherein the stent is radiopaque.

28. An expandable stent comprising:
a plurality of first expandable segments;
a plurality of second expandable segments;
a plurality of adjacent cylindrical main body elements having collinear cylindrical axes, the cylindrical main body elements formed by connecting first expandable segments with second expandable segments via substantially H-shaped connecting segments;
a plurality of first helical segments having a pitch, the first helical segments formed by connecting first expandable segments from adjacent cylindrical elements with each other; and
a plurality of second helical segments formed by connecting second expandable segments from adjacent cylindrical elements with each other, wherein the second helical segments have a pitch that differs from the pitch of the first helical segments.

29. The stent of claim 28, further comprising a first and second endzone, the first and second endzones straddling the main body.

30. The stent of claim 28, wherein at least one helical segment forms an angle of approximately 40° relative to the cylindrical axis of the stent.

31. The stent of claim 1, wherein each main body cylindrical element comprises:
   (1) a first plurality of the expandable circumferential segments and
   (2) a second plurality of circumferential segments, wherein the first and second pluralities of circumferential segments are joined to each other by the connecting-segment portions of the helical segments, thereby forming the cylindrical element, and further wherein the first and second pluralities Of circumferential segments comprise a majority of the circumference of each cylindrical element.

32. The stent of claim 31, wherein the first circumferential segments alternate with the second circumferential segments.

33. The stent of claim 31 or 32, wherein the circumferential dimensions of the first and second pluralities of circumferential segments are equal.

34. The stent of claim 31 or 32, wherein the circumferential dimension(s) of one or more of the second plurality of circumferential segments is/are larger than the circumferential dimensions of the first plurality of circumferential segments.

* * * * *

INTER PARTES REEXAMINATION CERTIFICATE (844th)
United States Patent
Addonizio et al.

(10) Number: US 7,329,277 C1
(45) Certificate Issued: Mar. 18, 2014

(54) STENT HAVING HELICAL ELEMENTS

(75) Inventors: Scott J. Addonizio, Fort Lauderdale, FL (US); David L. Camp, Jr., Hillsboro Beach, FL (US); Gary J. Becker, Miami, FL (US); John D. Pazienza, Pompano Beach, FL (US)

(73) Assignee: Orbusneich Medical, Inc., Fort Lauderdale, FL (US)

Reexamination Request:
No. 95/001,929, Mar. 23, 2012

Reexamination Certificate for:
Patent No.: 7,329,277
Issued: Feb. 12, 2008
Appl. No.: 10/014,705
Filed: Dec. 11, 2001

Related U.S. Application Data

(63) Continuation-in-part of application No. 09/511,481, filed on Feb. 23, 2000, now Pat. No. 7,108,714, which is a continuation of application No. 09/094,402, filed on Jun. 10, 1998, now Pat. No. 6,117,165.

(60) Provisional application No. 60/254,688, filed on Dec. 11, 2000.

(30) Foreign Application Priority Data

Jun. 13, 1997 (EP) .................................. 97201799
May 6, 1998 (EP) .................................. 98201446

(51) Int. Cl.
*A61F 2/06* (2013.01)

(52) U.S. Cl.
USPC ........................................ 623/1.22; 623/1.15

(58) Field of Classification Search
None
See application file for complete search history.

(56) References Cited

To view the complete listing of prior art documents cited during the proceeding for Reexamination Control Number 95/001,929, please refer to the USPTO's public Patent Application Information Retrieval (PAIR) system under the Display References tab.

*Primary Examiner* — Cary E. Wehner

(57) ABSTRACT

An expandable stent comprised of a plurality of helical segments is disclosed. In one embodiment, the stent is generally cylindrical in shape having a cylindrical axis, and comprises a first and second set of helical segments. The helical segments in the first set are substantially parallel and have a first pitch forming a first helical angle with respect to the cylindrical axis. The helical segments in the second set are also generally parallel to each other and form a second pitch that differs from the first pitch, thereby forming a second helical angle with respect to the cylindrical axis. In an alternative embodiment, the stent comprises one set of helical segments and a plurality of circumferential elements that are joined together by the helical segments to form a plurality of cylindrical elements which are joined together to form a stent body. The stent may also have endzones.

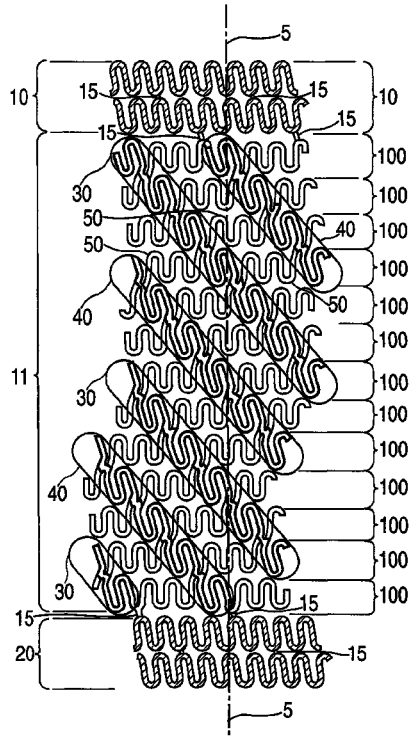

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-8, 10-29 and 31-34 are cancelled.

Claims 9 and 30 were not reexamined.

\* \* \* \* \*